US008831292B2

(12) United States Patent
Brueckner et al.

(10) Patent No.: US 8,831,292 B2
(45) Date of Patent: Sep. 9, 2014

(54) METHOD AND APPARATUS FOR THE OPTICAL EVALUATION OF HARVESTED CROP IN A HARVESTING MACHINE

(75) Inventors: Peter Brueckner, Suhl (DE); Steffen Lerm, Ilmenau (DE); Daniel Garten, Walldorf (DE); Silvio Holder, Schleusingen (DE)

(73) Assignee: Deer & Company, Moline, IL (US)

( * ) Notice: Subject to any disclaimer, the term of this patent is extended or adjusted under 35 U.S.C. 154(b) by 0 days.

(21) Appl. No.: 13/584,942

(22) Filed: Aug. 14, 2012

(65) Prior Publication Data

US 2014/0050364 A1   Feb. 20, 2014

(30) Foreign Application Priority Data

Sep. 19, 2011   (DE) .......................... 10 2011 082 908

(51) Int. Cl.
*G06K 9/00* (2006.01)
*A01D 41/127* (2006.01)
*G01N 21/00* (2006.01)
*G06K 9/34* (2006.01)

(52) U.S. Cl.
CPC ............ *A01D 41/1277* (2013.01); *G01N 21/00* (2013.01); *G06K 9/34* (2013.01)
USPC ...................................................... 382/110

(58) Field of Classification Search
None
See application file for complete search history.

(56) References Cited

U.S. PATENT DOCUMENTS

| | | | | |
|---|---|---|---|---|
| 5,841,883 A | * | 11/1998 | Kono et al. | 382/110 |
| 5,917,927 A | * | 6/1999 | Satake et al. | 382/110 |
| 6,285,198 B1 | * | 9/2001 | Nelson et al. | 324/664 |
| 6,731,793 B1 | | 5/2004 | Usbeck et al. | |
| 8,086,378 B2 | | 12/2011 | Behnke | |
| 8,531,733 B2 | * | 9/2013 | Fan et al. | 358/3.27 |
| 2005/0072135 A1 | * | 4/2005 | Kormann | 56/500 |
| 2008/0075385 A1 | * | 3/2008 | David et al. | 382/275 |
| 2010/0111369 A1 | * | 5/2010 | Lussier | 382/110 |
| 2010/0316294 A1 | * | 12/2010 | Perner | 382/173 |
| 2011/0282811 A1 | * | 11/2011 | Perner | 706/12 |
| 2013/0021469 A1 | * | 1/2013 | Conrad et al. | 348/135 |
| 2013/0235183 A1 | * | 9/2013 | Redden, Lee Kamp | 348/89 |

FOREIGN PATENT DOCUMENTS

| | | | |
|---|---|---|---|
| DE | 102004063769 A1 | 7/2006 | |
| EP | 0908086 A1 | 9/1997 | |
| EP | 2057882 A2 | 5/2009 | |

OTHER PUBLICATIONS

European Search Report, dated Dec. 6, 2013 (8 Pages).

* cited by examiner

*Primary Examiner* — Tahmina Ansari

(57) ABSTRACT

An arrangement for the optical evaluation of harvested crop in a harvesting machine includes a camera located for taking images of threshed out crop elements (grain and material other than grain) being conveyed within a channel of the machine. An electronic image processing system receives the images and identifies individual objects in the images, these objects being classified into predetermined object classes by way of comparing at least one of color, contour or texture features of the individual objects and corresponding characteristics of reference objects filed in a data bank. The processing system then determines the absolute or relative numbers or areas of the individual objects assigned to the respective object classes.

14 Claims, 4 Drawing Sheets

METHOD AND APPARATUS FOR THE OPTICAL EVALUATION OF HARVESTED CROP IN A HARVESTING MACHINE

RELATED APPLICATIONS

This application claims priority under 35 USC 119 to DE 10 2011 082 908.3 which was filed Sep. 19, 2011.

FIELD OF THE INVENTION

The present invention relates to a method for the optical evaluation of harvested crop.

BACKGROUND OF THE INVENTION

Combine-harvesters are large machines which harvest grain from a field, thresh it and clean it. A combine-harvester includes a number of adjustable elements, such as the size of the openings of a threshing basket or of a separating screen, the size of a threshing gap, the speed of a threshing drum, the speed of a cleaning blower or the position of slats of a sieve. The optimum operating parameter of said elements depends on the type of harvested crop and the characteristics thereof and can change over time. The adjustment of said parameters is usually carried out by the operator of the combine-harvester on the basis of operating instructions or his experience or it is carried out automatically using values which are filed in a memory and which are called up by the operator as a function of the current conditions of the surrounding area and of the harvested crop. In the past, many sensors have been proposed to detect the characteristics of the harvested crop (such as capacitive moisture sensors, cameras and near infrared spectrometers) in order to detect harvested crop characteristics on board the combine-harvester and to give the operator an indication concerning the characteristics of the harvested crop present at that time after processing in the harvesting machine, on the basis of which he (or an independent control means) is able to modify parameters of the processing process in the harvesting machine. Thus, for example, he can enlarge the threshing gap and reduce the speed of the threshing drum if the proportion of broken grain is too high.

A camera, which, for example, takes an image of the cleaned grain before it passes into the grain tank, or an image of the material in the returns conveyor which supplies harvested crop from the rear end of a sieve back to the threshing operation or to a separate finishing thresher, is particularly suitable to obtain information for the manual or automatic adjustment of parameters of the processing process of a combine-harvester. As an unprocessed image is hardly meaningful in particular to operators with little experience, the image, as a rule, is processed by means of an electronic image processing system in order to indicate to the operator, on the one hand, certain particles, such as broken grain or contaminants in the image shown of the harvested crop in colour or highlighted in another manner and, on the other hand, to be able to display quantitative sizes (for example with regard to the proportion of broken grain and/or contaminants). The quantitative sizes can, as already mentioned, be used for the manual or automatic adjustment of parameters of the processing process in the harvesting machine.

EP 2 057 882 A2 describes a combine-harvester with such an image processing system which initially carries out a brightness match on the recorded digitalized image data. The image is then subjected to segmenting, which can be targeted at individual objects and/or individual object edges. In the case of such targeted segmenting, the image is divided into individual objects defined by brightness or colour values which are identical per se. By way of comparison between the brightness of the respective region and a required value or a mean value for the brightness of the image, it is concluded whether the region represents a broken grain. The area of the broken grain is determined by counting the pixels of the region and the proportion of broken grain is evaluated by way of comparison with the number of pixels in the image. Edge-oriented segmenting serves to identify broken grain and is based on an evaluation of the lengths of the boundaries of the individual objects. Where the object is sufficiently large, it is assumed that it is a short piece of straw. The areas of the objects identified as short straw are also compared in relation to the size of the entire image in order to determine the proportion of contaminants. The assignment of the image objects to the "broken grain" or "short straw" classes is effected accordingly simply by way of the brightness of the individual objects or of their length. In this connection, inaccuracies can hardly be avoided because, for example, it is not possible to determine short straw particles which are smaller than the grains. In an analogous manner, broken grains with broken areas which do not lie head-on to the camera are not differentiated from intact grain.

U.S. Pat. No. 5,917,927 A1, which is viewed as generic, describes a stationary arrangement for determining the proportion of broken grains of rice where the dimensions (length, width and area) and possibly also other dimensions of each grain are determined from the image taken. Classification of the grain is effected by comparison with data from a table, in which simulated or currently measured data for grain is filed, which is called up by way of combinations of features of the respective grain to be inspected. Here too the classification is effected only by way of the dimensions of the respective object, which involves the disadvantages already mentioned in the preceding paragraph.

SUMMARY OF THE INVENTION

According to the present invention, there is provided an improved method and apparatus for optically evaluating harvested crop in a harvesting machine.

It is the object of the present invention to provide a method, improved compared to the prior art, for the optical evaluation of harvested crop in a harvesting machine and a corresponding arrangement where the abovementioned disadvantages are not present or are present to a reduced extent.

This object is achieved by the teachings of Claims 1 and 12, the subordinate claims describing advantageous embodiments.

In the case of a method and an arrangement for the optical evaluation of harvested crop, an image of the harvested crop is initially recorded with a camera such that an electronic image processing system (online) has a digital image of the harvested crop. The image processing system then identifies individual objects in the image and, by means of the image processing system by way of comparison between colour features and/or contour features and/or texture features of the individual objects and corresponding characteristics of reference objects filed in a data bank, classifies the individual objects into predetermined object classes. The absolute and/or relative numbers and/or areas of the individual objects assigned to the respective object classes are calculated and preferably finally displayed on a display device and/or made known in another manner, e.g. acoustically.

The comparison between the reference objects in the data bank and the individual objects in the recorded image is effected not only by way of the dimensions of the objects as is known in the art, but also by way of the colour, the contour (the shape) and/or the texture of the objects. In this case, for example, use is made of the fact that straw and chaff generally have a colour other than that of the pure grains, and the colour of the broken areas of grains is once again different to that of undamaged grains. In an analogous manner, the straw particles generally have rectangular contours with ragged torn edges, whereas grains have a rather round or oval form, which is not completely present in the case of broken grains. The texture of the pure grains is generally relatively uniform, whereas straw is often provided with longitudinal strips. Consequently, a number of characteristics of the individual objects are compared with the characteristics of the reference objects, which, in particular as they are complete, allow for non-problematic identification and classification. As a result, it is possible to classify the objects into the individual classes in a considerably more accurate manner, because by way of a combination from a larger number of features, the individual objects can be classified better and more accurately than before. The operator of the harvesting machine is consequently provided with information as to how high a proportion of the respective object classes is in the harvested crop, where in the case of a combine-harvester, for example, this can be broken grain or foreign objects (contaminants) or non-threshed grains. On the basis of said proportions, the operator is able to adapt adjustments of parameters of the processing process in the harvesting machine and/or a control means can adapt parameters of the processing process in the harvesting machine in order to optimize the work of the combine-harvester The data bank preferably contains characteristics of manually classified reference objects which have been recorded by way of real harvested crop, and the associated manual classification by an expert. Prior to use on the machine, a data bank is created (training) on the basis of the images of known objects. Consequently, by means of the image processing system, the operator of the machine has the comparative information necessary for the recognition immediately available.

As different types of harvested crop (e.g. wheat, barley or corn) also implies different reference objects, an obvious thing to do is to collect characteristics of reference objects of different types of harvested crop into the data bank. The image processing system is provided (for example by the operator by means of an input device or a suitable sensor or by comparison between camera images and reference images of different types of harvested crops) with information with regard to the type of the harvested crop already inspected in each case, by way of which it selects the characteristics of the reference objects of the respective harvested crop from the data bank.

The percentage area determined in the image or the number of objects per class is output as a percentage for the individual classes. In addition, the data bank can include correction factors, by way of which the numbers of the individual objects assigned to the respective object classes can be converted into mass percentages. The mass of individual classes can be estimated and output by means of the class-specific correction factors. A conversion of the analysis results into mass percentages usual in the industry is consequently achieved. The correction factors are deposited in the data bank and as a rule have been determined beforehand by means of empirical tests.

In the case of the image pre-processing, the image can be brightness scaled initially by way of global image and local image intensities.

The image is preferably divided up into individual objects and background by means of a binary cutting mask and only the individual objects are processed further.

The individual objects can be processed further in a size-dependent manner by individual objects lying below a threshold value of one or several dimensions being treated as background and/or individual objects lying above a threshold value of one or several dimensions being divided up into several individual objects by local brightness scaling and an application of a cutting mask with sharper discrimination parameters than in the case of the previous application of the cutting mask. Various part process steps, which reject non plausible individual objects and/or merge at least two or more individual objects by way of specific individual object features, then follow. Through the individual objects of the cutting mask reworked in this manner, the individual objects can be cut out of the original image by means of coordinates of the cutting mask and all the pixels alien to the object in the individual object image are represented therein by a neutral colour dot. Several features are then calculated as a last block in the multi-channel individual object and are classified by access to a data bank. The result of the classification is then made available to the operator in a suitable form.

The results are made available to the operator as digital and/or graphic statistics, preferably as a bar chart. The operator is able to vary the control elements of the harvesting machine by way of this information. In addition, the image from the camera can be displayed on a display device and independent of the calculated object class, colour marked representations of the identified individual objects can be superposed. The analysis result is accordingly made available to the operator as an overlay image. Colours are assigned to the individual classes and as an option placed as a semi-transparent layer over the image that is fundamental to the calculation. The operator can consequently recognize whether the assignment of the individual objects to the individual object classes is effected correctly and decide how good the calculation of the cutting mask and the classification of the extracted individual objects is and consequently, where applicable, adapt parameters of the algorithm by changing, e.g. the brightness threshold, from which an individual object is recognized as such, or the size from which an individual object is no longer deemed to be background in order to optimize the image processing process. Should parameters of the algorithm be changed by the operator, a further analysis of the identical image and the representation of the result are thus effected. In this way, the operator can improve the recognition quality manually by trial and error with no knowledge of the analysis sequence.

These and other objects, features and advantages of the present invention become obvious to the person skilled in the art after reading the following detailed description and in view of the drawings.

DESCRIPTION OF THE PREFERRED EMBODIMENT

Figure 1:
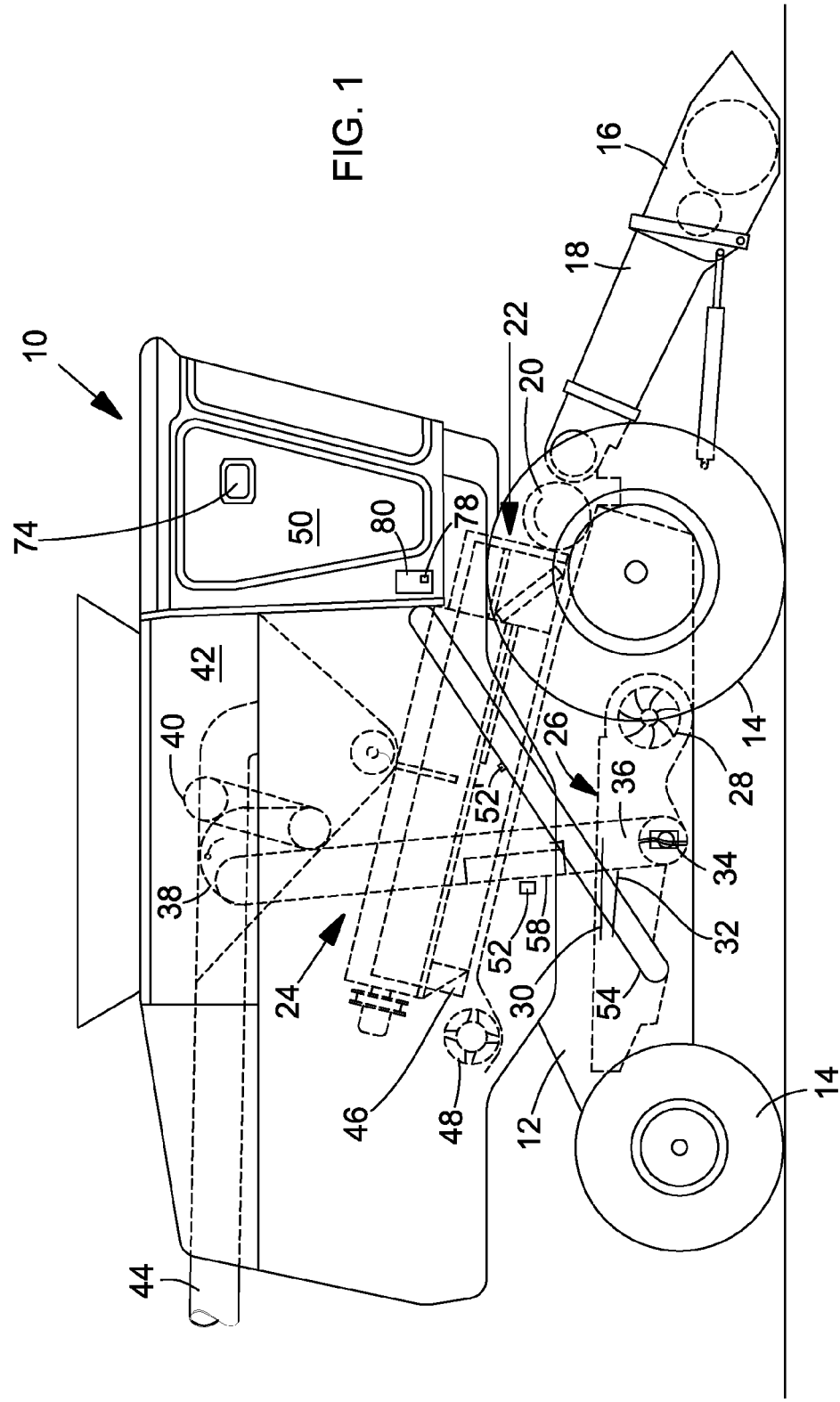
FIG. 1 is a side view of a harvesting machine.

Reference is now made to FIG. 1 which shows an agricultural harvesting machine in the form of a combine-harvester 10, which includes a main frame 12 with driven front and steerable rear wheels 14 in contact with the ground, which wheels support the main frame 12 for forward movement over a field to be harvested. Although wheels 14 are shown, the combine-harvester 10 can be supported completely or in part by caterpillar running gear which is in contact with the ground. The drive of the front wheels 14 is effected by means of a conventional hydrostatic transmission from a combustion engine fastened on the main frame. Directional specifications (such as forward) below relate to the forward direction of the combine-harvester 10, which moves to the right in FIG. 1.

A vertically adjustable harvest attachment in the form of cutting gear 16 is used in order to harvest crop and supply it to a slope conveyor 18. The slope conveyor 18 is pivotably mounted on the main frame 12 and includes a conveyor in order to supply the incoming harvested crop to a directing drum 20. The directing drum 20 conveys the harvested crop upward through an inlet transition portion 22 to a rotating threshing and separating assembly 24. Other orientations and types of threshing structures and other types of harvest attachments 16 can also be used, such as a transversely extending frame which supports individual row units.

During the harvesting operation, the rotating threshing and separating assembly 24 threshes and separates the harvested crop. Grain and chaff fall through grids on the floor of the rotating threshing and separating assembly 24 into a cleaning system 26. The cleaning system 26 includes a blower 28, upper sieve 30 and lower sieve 32 which separate off the chaff. The clean grain is brought together over the width of the cleaning system 26 by means of a cross conveyor screw 34, which supplies it to an elevator 36 for clean grain. The elevator 36 includes chains and paddles and conveys the clean grain into a transition portion 38, proceeding from where it is conveyed by a grain tank fill screw 40 into a grain tank 42. The clean grain in the grain tank 42 can be offloaded by an unloading screw conveyor 44 onto a grain truck or lorry. Returns are returned from the rear end of the bottom sieve 32 to the rotating threshing and separating assembly 24 by means of a returns elevator 54.

Threshed-out, separated straw is transferred from the rotating threshing and separating assembly 24 to a discharge conveyor 48 by means of an outlet 46. The discharge conveyor ejects the straw out of the rear of the combine-harvester 10. It must be noted that the discharge conveyor 48 could supply the material that is not grain directly to a straw cutter. The operation of the combine-harvester 10 is controlled from inside an operator's cabin 50.

An image recording system 52 is provided for the optical inspection of the harvested crop and for the evaluation of the threshing, separating and cleaning process of the combine-harvester 10 based thereon. It can be arranged on the run-up side of the elevator 36 and there can monitor the flow of the grain into the grain tank 42 or can be positioned in the form of image recording system 52' on the returns elevator 54 and there can monitor the returns harvested crop flow. It would also be conceivable to attach an image recording system (not shown) on a measuring chamber, into which the harvested crop is filled intermittently and removed therefrom again, as is shown in U.S. Pat. No. 6,285,198 B1 or EP 0 908 086 A1.

Figure 2:
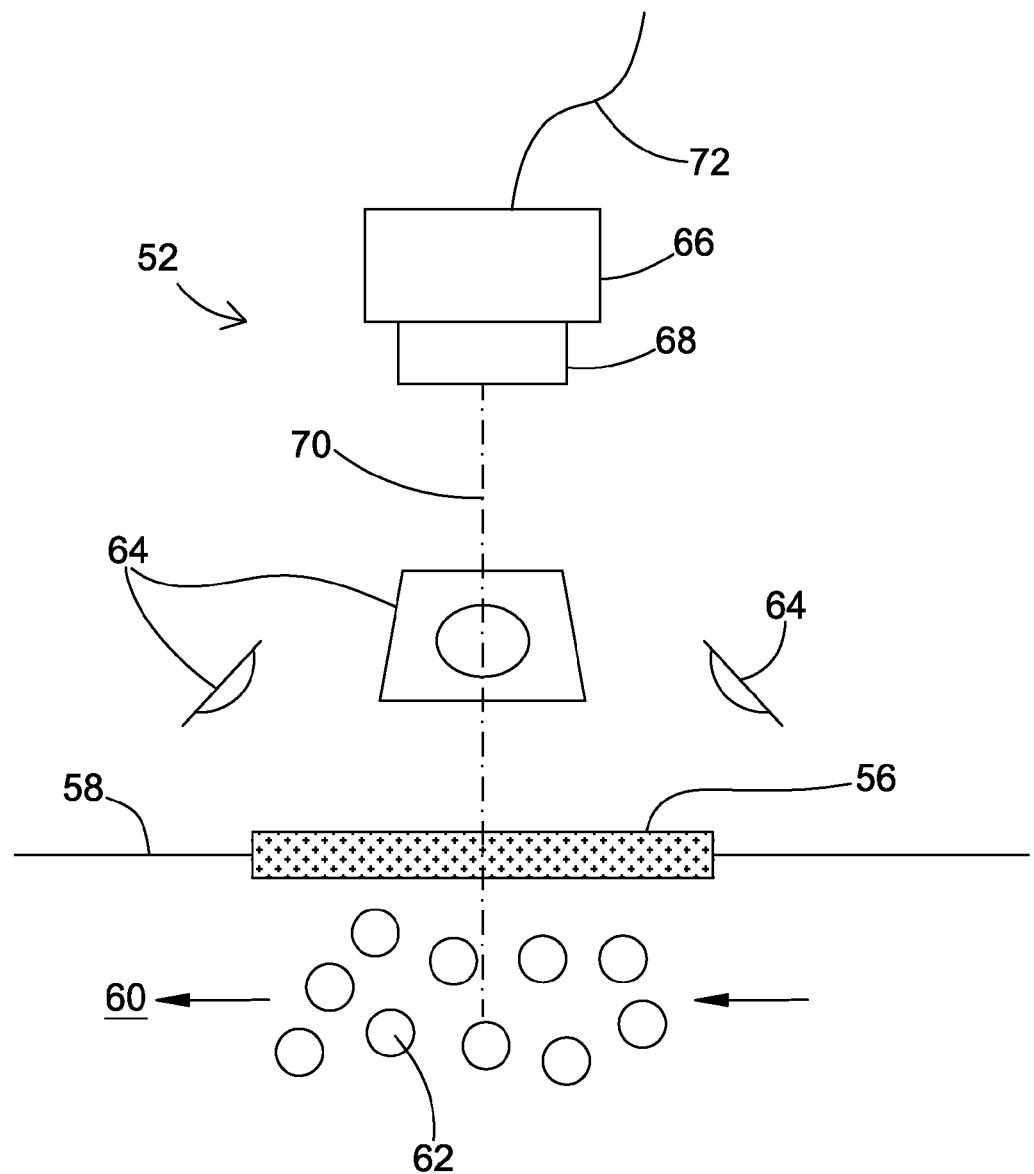
FIG. 2 is a schematic view of an image recording system.

Referring to FIG. 2, it can be seen that the image recording system 52 includes a disc 56 which is transparent to visible light and is inserted into a wall 58 of a channel 60 of a conveying device conveying the harvested crop 62, in this case the elevator 36 or the returns elevator 54. The disc 56 is provided on one or both sides with an antireflective coating in order to avoid unwanted blooming. The harvested crop 62 is illuminated by several light sources 64 which are distributed in a circular manner about an optical axis 70 of the disc 56. The light sources 64 can be realized as bulbs, flashing lights, annular flashing lights or preferably as light diodes. The light sources 64 are inclined at an angle with respect to the optical axis. A lens 68 of a camera 66 is also arranged on the optical axis 70 of the disc 56 and is focussed on the harvested crop 62 in the channel 60.

The camera 66 has a digital output which is connected by means of a cable 72 to an electronic image processing system 80 which is connected, in its turn, to a display device 74.

Figure 3:
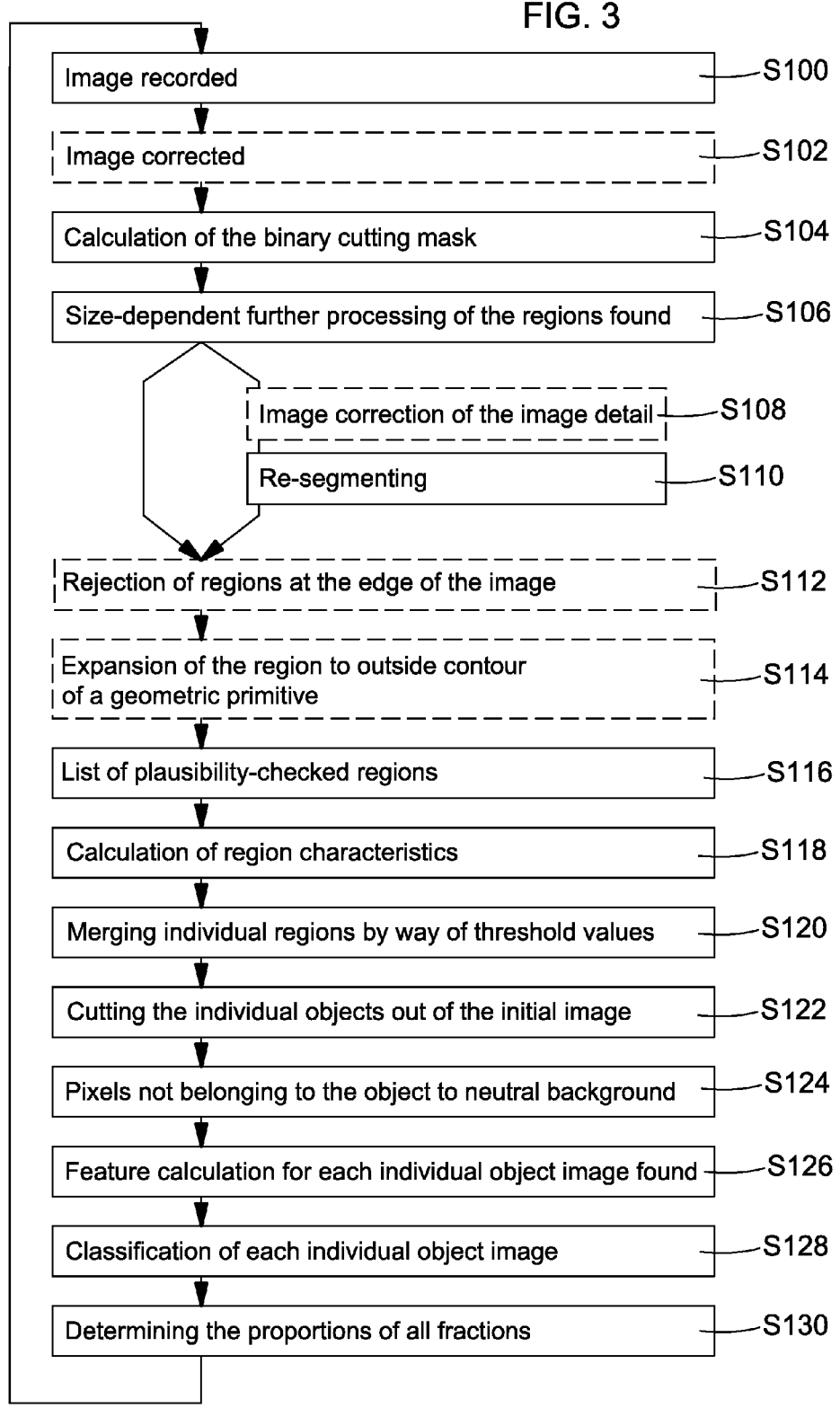
FIG. 3 shows a flow diagram, according to which the image processing system operates.

FIG. 3 shows a flow diagram, according to which the image processing system 80 operates. It includes the following steps:

a) Recording the harvested crop by an image sensor of the camera (S100)
b) Image correction to compensate for inhomogeneties (S102)
c) Calculation of a binary cutting mask which separates the initial image into objects and background (S104)
d) Size-dependent further processing of contiguous individual objects in the cutting mask (S106)
e) Calculation of a cutting mask with sharper discrimination parameters than in the case of the first application by means of the pre-processing of the image detail in order to divide up large individual objects into several individual objects (S108 to S110)
f) Optional rejecting of individual objects at the image edge (S112)
g) Optional expansion of the outside contour of the found region by a circumscribing traverse (S114)
h) Creating a list of valid objects which are tested by several plausibility checks (S116)
i) Calculating individual object characteristics and, where applicable, merging of individual objects by way of threshold values (S118 to S120)
j) Cutting individual objects out of the original camera image by way of the coordinates of the individual objects (S122) extracted from the cutting mask and reworked into steps d to i) and colouring all the pixels that do not belong to the object in a neutral colour (S124)
k) Determining colour, texture and contour-based image features with subsequent classification by using individual values from the data bank (S126 to S128)
l) Calculating the proportions of objects classified to the classes "perfect", "broken", "light unwanted particles", "heavy unwanted particles", "non-threshed unwanted particles" and "incorrectly cut out and/or non classifiable objects" (S130).

Individual regions and individual objects are deemed to be synonymous in the Figures and in the entire description.

The proportions calculated in step l) (S130) are made available to the operator on the display device 74 in the cabin, he is then able to adapt the operating parameters of the combine-harvester by way of current analysis results. When in step l an unwanted proportion with a limit value determined in advance is exceeded, an alarm signal is sounded to the operator in order to ask him to adjust a harvesting machine operating parameter. It would also be possible for the adjustment of an operating parameter to be effected in an automatic manner.

The present method is suitable for any harvesting and processing machine where it is possible to make images of the harvested crop volume flow.

The (optional) image correction from step b) (S102) is based on a renormalization of the original camera image by way of global image and local image intensities. The information for classification of the objects lies in the relative change in intensity of adjacent pixels. Consequently, the absolute size of the relative change in intensity is not relevant, but rather the relative signature of the grains in the intensity profile is relevant. For this reason the camera image is pre-processed for further processing steps. The mean value image of the camera image and the average intensity of each colour channel is calculated for this purpose. The filter size of the mean value image, in this case, is adapted to the objects in the image. The pre-processed image is produced by adding the average intensities per colour channel and the difference to the mean value filtered image. The calculation of the corrected image consequently requires no reference images whatsoever and can be carried out on each individual image. In this case, the image can be both monochrome and multi-channel. It is also possible to correct only selected colour channels. The correction is helpful to the colour intensity and contour dependent calculation of the cutting mask according to step c) (S104).

The aim of the calculation of the binary cutting mask according to step c) (S104) is to reduce the data set of each and every pixel. Originally, colour or multi-channel intensities are processed with the design-dependent bit depth of the camera. The aim of the segmenting is a reduction in the data from n channels to a binary statement, whether the current pixel belongs to an object or not. Consequently, the initial image is converted into a monochrome image by a dimension-reducing transformation. In addition, the 2D vector difference image (cf. U.S. Pat. No. 6,731,793 B1) of the initial image is calculated. This is subtracted from the monochrome image in order to strengthen the edges. The difference image is consequently generated. The cutting mask is produced from a comparison between the mean value filtered difference image and the product of a discrimination parameter and the difference image itself. The filter size of the mean value image is adapted to the image content. The result is a binary cutting mask. The uninteresting background is "false", segmented objects being "true".

The individual objects of the cutting mask found in this manner are then processed further in a side-dependent manner according to step d) (S106). Individual objects that are too small and consequently not plausible or punctiform or linear individual objects are rejected. Normal size individual objects are stored. Individual objects that are too large are (in the optional steps S108 to S110) separated by local re-segmenting by means of a new calculation of a local image correction (to step S102) and a local calculation of the binary cutting mask with other sharper parameters (corresponding to step S104). The large individual objects separated off in this manner are rejected and simply the (part) individual objects found from the re-segmenting are stored. In step S112, individual objects which lie at the image edge are optionally rejected as said objects have not been completely detected with the camera and so are not clearly classifiable.

Should the segmenting not function satisfactorily due to inner and/or outer disturbance variables, optional expansion of the individual object outside contour can be activated, see S114. This expands the outside contour of the region to a circumscribing polygon and consequently smoothes ragged contour data.

Consequently, pre-selected individual objects, which are subject to further plausibility checks, are produced for step S116. The result of step S116 is a list of valid plausibility-checked individual objects which are processed further.

From all the checked and plausible individual objects, further features such as, for example the position of the centre of gravity and orientation are calculated. Individual objects are summarized, where applicable, by way of said features. This occurs in steps S118 to S120. If a further individual object centre of gravity is situated in the vicinity of the region currently to be inspected and if the respective orientations are similar to each other, the point clouds of both individual objects are combined and a new region is generated in this manner. The two parent individual objects are rejected once all the important metadata has been transferred to the child individual object.

Figure 4:
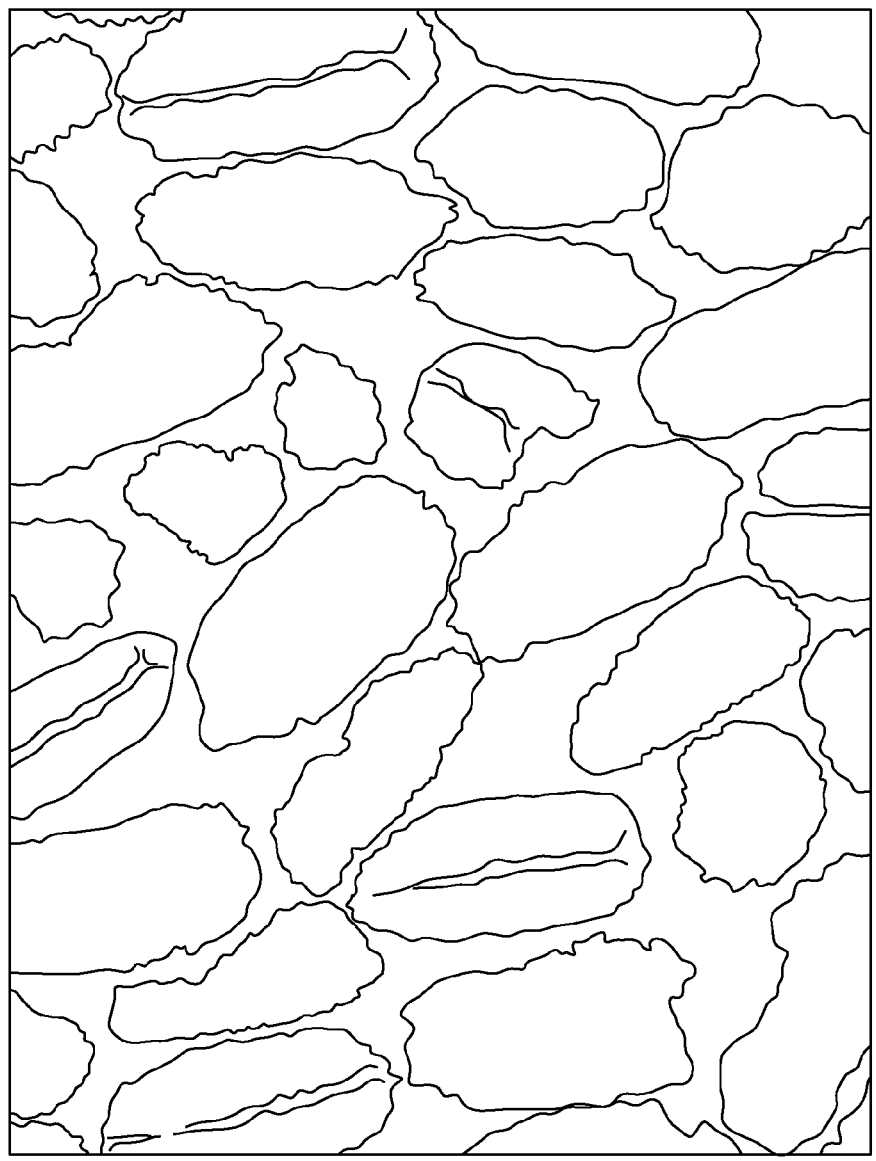
FIG. 4 shows a camera image with representation of the identified objects.

All the plausible individual objects of an image stored in this manner (cf. the example shown in FIG. 4) serve in the following step 122 to cut the original objects out of the recorded camera image. Through the rectangular organisation of image data in data processing devices, a circumscribing rectangle of the region is applied as the image. The image is referred to as the individual object image. All the pixels of the individual object image have associated therewith the colour values according to the colour camera image and the coordinate list of the pixels of the cutting mask. Pixels of the individual object image, which, corresponding to the corresponding region of the cutting mask, do not belong to the individual object, are shown in step S124 by a neutral colour dot. The neutral colour dot does not influence the classification in the following classification step (S126, S128).

During classification, a relatively high number of features of each found individual object image are initially identified in step S126. These features are divided among other things into the categories of colour features, contour features and texture features. Feature vectors from each class are available for classification by way of a data bank 78 (see FIG. 1) with individual object images from each class classified manually once in advance. By way of said feature vectors, each object can now be divided in step S128 into the classes (e.g. "perfect", "broken", "light unwanted particles", "heavy unwanted particles", "non-threshed unwanted particles" and "incorrectly cut out and/or not classifiable objects"). The calculation of the respective proportions of each class is then effected (S130). In this case, the absolute numbers of the objects in the individual classes can be determined and displayed, i.e. the total number of objects of the class in one image, or their relative numbers, i.e. the total number of objects of the class in an image divided by the total number of objects in the image. The absolute areas of objects can also be determined and displayed, i.e., the added areas of the total number of objects of the class in one image, or their relative percentage areas, i.e., the added areas of the total number of objects of the class in one image divided by the added areas of objects in the image.

By means of the analysis of one or several camera images, as an alternative to this on a number of camera images determined in advance or a time segment determined in advance, in each case the current analysis result is made available to the operator. As a result, the operator is able to recognize whether his changes to the operating parameter of the harvesting or processing machine are productive or the relative object composition has changed in a negative manner. In addition, it is possible to take changing plants into consideration by means of a cyclical analysis representation. Not all plants supply a harvested crop of equal quality, which can now be evaluated in a more selective manner by means of the invention.

Having described the preferred embodiment, it will become apparent that various modifications can be made without departing from the scope of the invention as defined in the accompanying claims.

The invention claimed is:

1. A method for the optical evaluation of harvested crop, said method including the following steps:

a) recording an image of the harvested crop (62) in a channel (50) within a harvesting machine (10) with a camera (66);
b) identifying individual objects in the image by means of an electronic image processing system (80) by dividing the image into individual objects and background by means of a binary cutting mask;
c) processing further the individual objects in a size-dependent manner, wherein:
  i) individual objects having at least one dimension below a threshold value being treated as background,
  ii) and individual objects having at least one dimension above a threshold value being divided up into several individual objects by local brightness scaling and an application of the cutting mask with sharper discrimination parameters than during the first application of the cutting mask in step b)
  iii) and the center of gravity and the respective orientations of the individual objects are inspected and the point clouds of two individual objects are merged if the center of gravity of another single object is in the vicinity of a region currently to be inspected and the respective orientations are similar;
d) classifying, by means of the image processing system (80), the individual objects into predetermined object classes by way of comparison between characteristics of the individual objects and characteristics of reference objects filed in a data bank (78), wherein the characteristics of the individual objects compared during classification include at least one of color features, contour features and texture features of the individual objects; and e) determining the absolute or relative numbers or areas of the individual objects assigned to the respective object classes.

2. The method according to claim 1, wherein the data bank (78) includes characteristics and the associated classification of manually classified reference objects, which were collected by examining real harvested crop.

3. The method according to claim 1, wherein the data bank (78) includes characteristics of reference objects of different types of harvested crop and information with regard to the type of harvested crop being inspected in each case is supplied to the image processing system (80), by way of which it retrieves from the data bank (78) those characteristics relating to the type of harvested crop being inspected.

4. The method according to one of claim 3, wherein the data bank (78) additionally includes correction factors, by way of which the numbers of the individual objects assigned to the respective object classes are converted into mass percentages.

5. The method according to claim 1, wherein the image is initially brightness scaled by way of global image and local image intensities and is consequently pre-processed.

6. The method according to claim 1, wherein the binary cutting mask is calculated by a comparison between a mean-filtered difference image and the product of a discrimination parameter and of the difference image itself, wherein the difference image describes the difference between the Y-transformation of the pre-processed camera image and a two-dimensional vector difference image of the camera image.

7. The method according to claim 1, wherein determined individual objects located at the edge of the image are rejected.

8. The method according to claim 1, wherein the segmented individual objects are reworked within the binary cutting mask in such a manner that the outside contour of the extracted individual objects is expanded by a traverse.

9. The method according to claim 1, wherein individual objects of the binary cutting mask are merged and consequently summarized for the purpose of process optimization by way of determined characteristics and determined threshold values.

10. The method according to claim 1, wherein the image from the camera (66) is displayed on a display device (74) and superposed with representations of the identified individual objects which are color-marked in dependence on the selected object class.

11. The method according to claim 1, wherein the determined composition of the harvested crop is displayed at least one of digitally or graphically on a display device (74).

12. An apparatus for the optical evaluation of harvested crop (62) being transported by an elevator (36 or 54), said apparatus including: a camera (66) arranged for recording an image of the harvested crop (62) in a channel (60) within a harvesting machine (10); an image processing system (80) coupled for receiving said image from said camera (66); a data bank (78) forming part of said image processing system (80) and containing information concerning the characteristics of reference objects; said image processing system (80) being operable for identifying individual objects in the image and to classify the individual objects into predetermined object classes by way of comparison between characteristics of the individual objects and characteristics of reference objects filed in the data bank (78); and an output device (74) being coupled to said image processing system (80) and being operable to output at least one of absolute or relative numbers or areas of the individual objects assigned to the respective object classes, wherein said characteristics comprise at least one of color features, contour features or texture features of the individual objects.

13. The apparatus according to claim 12, wherein the image recording system (52) includes a disc (56) which is transparent at least to visible light and is inserted into a wall (58) of a channel containing harvested crop (62); said disc (56) being provided on one or both sides with an antireflective coating in order to avoid unwanted blooming; several light sources (64) defined as a plurality of light diodes being distributed in a circular manner about, and inclined relative to an optical axis (70) of the disc (56) so as to illuminate the harvested crop (62); said camera (66) having a lens (68) located on the optical axis (70) of the disc (56) and focussed on the harvested crop (62) in the channel (60).

14. The apparatus according to claim 13, wherein the transparent disc (52) is transparent to at least one of ultraviolet radiation or to radiation within the near infrared range.

* * * * *